US009277862B2

(12) United States Patent
Rao et al.

(10) Patent No.: US 9,277,862 B2
(45) Date of Patent: Mar. 8, 2016

(54) METHOD AND SYSTEM TO IDENTIFY INTRAOCULAR PRESSURE (IOP) OF AN EYE

(75) Inventors: Shyam Vasudeva Rao, Karnataka (IN); Kuppuswamy Chandrasekhar, Karnataka (IN); Mahabaleswara Ram Bhatt, Karnataka (IN)

(73) Assignee: FORUS HEALTH PVT. LTD., Bangalore, Karntaka (IN)

( * ) Notice: Subject to any disclaimer, the term of this patent is extended or adjusted under 35 U.S.C. 154(b) by 185 days.

(21) Appl. No.: 14/114,917

(22) PCT Filed: Aug. 14, 2012

(86) PCT No.: PCT/IB2012/054134
§ 371 (c)(1),
(2), (4) Date: Oct. 31, 2013

(87) PCT Pub. No.: WO2013/024431
PCT Pub. Date: Feb. 21, 2013

(65) Prior Publication Data
US 2014/0066742 A1  Mar. 6, 2014

(30) Foreign Application Priority Data
Aug. 18, 2011 (IN) .......................... 2831/CHE/2011

(51) Int. Cl.
*A61B 3/16* (2006.01)
(52) U.S. Cl.
CPC ...................................... *A61B 3/165* (2013.01)
(58) Field of Classification Search
CPC ............. A61B 3/165; A61B 3/16; A61B 3/18
See application file for complete search history.

(56) References Cited

U.S. PATENT DOCUMENTS

| | | | | |
|---|---|---|---|---|
| 3,585,849 A | * | 6/1971 | Grolman | 600/401 |
| 4,172,447 A | * | 10/1979 | Bencze et al. | 600/401 |
| 4,724,843 A | * | 2/1988 | Fisher | 600/401 |
| 4,944,303 A | * | 7/1990 | Katsuragi | 600/401 |

(Continued)

OTHER PUBLICATIONS

Kyoung Hwan Kim et al: "Intraocular pressure measurement devices using the micro reflected air pressure sensor for the pre-diagnosis of the glaucoma," Nanotechnology (IEEE-NANO), 2010 10th IEEE Conference on, IEEE, Piscataway, NJ, USA, Aug. 17, 2010, pp. 907-910, XP031857562, ISBN: 978-1-4244-7033-4.

(Continued)

*Primary Examiner* — Adam J Eiseman
*Assistant Examiner* — Yasmeen S Warsi
(74) *Attorney, Agent, or Firm* — Harness, Dickey & Pierce, P.L.C.

(57) ABSTRACT

Non-tactile and non-evasive tonometer utilizing air flow with a definite amount of pressure to the eye and a mechanism to deflate the thin foil set that is placed near to eye ball such that re-bounded air hits on it. The mechanism involves acquiring or capturing then the images of the known pattern marking on thin foils both before and after deflating process due to rebounded air. On evaluating the deformation of the pattern appearing in the images obtained before and after air flow and calibrating the deformation with respect to size, translation, rotation and scaling parameters due the different pressure level that hits the eye ball and that rebounds on to thin foils, we arrive at a scheme of measuring the intraocular pressure of human eye. This intraocular pressure is used as a parameter for the ophthalmologist to diagnose glaucoma impairment of human beings.

14 Claims, 8 Drawing Sheets

(56) References Cited

U.S. PATENT DOCUMENTS

| | | | |
|---|---|---|---|
| 4,996,990 A * | 3/1991 | Hideshima | 600/401 |
| 5,830,139 A * | 11/1998 | Abreu | 600/405 |
| 5,964,704 A * | 10/1999 | Hayafuji | 600/401 |
| 6,042,544 A * | 3/2000 | Miwa et al. | 600/399 |
| 6,053,867 A * | 4/2000 | Iijima | 600/399 |
| 6,120,444 A * | 9/2000 | Miyakawa et al. | 600/401 |
| 6,190,317 B1 * | 2/2001 | Hayafuji | 600/405 |
| 2002/0049373 A1 * | 4/2002 | Miwa | 600/401 |
| 2011/0118585 A1 * | 5/2011 | Ishii et al. | 600/401 |

OTHER PUBLICATIONS

International Search Report and Written Opinion for PCT/IB2012/054134, mailed Nov. 29, 2012; ISA/EP.

* cited by examiner

METHOD AND SYSTEM TO IDENTIFY INTRAOCULAR PRESSURE (IOP) OF AN EYE

CROSS-REFERENCE TO RELATED APPLICATIONS

This application is a 371 U.S. National Stage of International Application No. PCT/IB2012/054134, filed Aug. 14, 2012, and claims priority to Indian Patent Application No. 2831/CHE/2011, filed Aug. 18, 2011, the disclosures of which are herein incorporated by reference in their entirety.

TECHNICAL FIELD

The present disclosure relates to a medical device. More particularly, embodiments relates to a method and a system for determining Intraocular Pressure (IOP) of an eye.

BACKGROUND

There are few non-contact and non-evasive Tonometers that utilize angle modulation of high frequency sound waves or light waves to determine the Intraocular Pressure (IOP) of a human eye using either frequency or phase modulation.

One of the limitations of aforementioned approaches is that the Intraocular Pressure parameter is intended to diagnose Glaucoma impairment but this need to be used in conjunction with other observations. Some of the other observations involved are based on image analysis of optic nerve head and retinal nerve fibre loss in the retinal portion of the eye. On this context, it is preferable to integrate these measurements into single device in order to avoid usage of multiple devices. As indicated earlier the Tonometer exploits either sound or light waves which demands different sources and measuring techniques, whereas, an imaging requires other type of sources and components. This leads to not only in increased bill of materials for the device but also to aid making device more portable.

Hence, there exists need to provide a system to integrate all measurement in a single device to reduce bill of materials for the device. Also, eliminate different sources and measuring techniques to measure IOP.

SUMMARY

The shortcomings of the prior art are overcome through the provision of a method and a system as described in the description.

Accordingly, the present disclosure relates to a method to identify Intraocular Pressure (IOP) of an eye by blowing air onto an eye ball of the eye. The method comprises of placing a foil-flap support assembly between an imaging unit and the eye, wherein the foil-flap support assembly has a transparent stiff foil fixed to a support and plurality of movable flaps facing the eye is suspended from the support. Once the foil-flap support assembly is placed, air of predetermined amount of pressure is blown onto an eye ball of the eye through an air channel, wherein the air blown to the eye ball rebounds from the eye ball deflating the flaps of the foil-flap support assembly. At this stage an image of the deflated foil-flap support assembly is captured and plurality of parameters value of the captured image is calculated. Now, the calculated plurality of parameters value is compared with plurality of predetermined parameters value to identify IOP of the eye.

A system to identify IOP of the eye is disclosed as another aspect of the present disclosure. The system comprises a foil-flap support assembly and a control unit. The foil-flop support assembly comprises a transparent stiff foil fixed to a support and plurality of movable flaps facing the eye is suspended from the support. The control unit comprises an imaging unit, a computing unit, a storage unit and a blowing unit. The blowing unit comprising an air channel is used to blow air of predetermined amount of pressure onto an eye ball of the eye. Thus, the blown air gets rebound deflating the flaps of the foil-flap support assembly. The imaging unit is used to capture image of the foil-flap support assembly before and after deflation of the flaps. The computing device is configured to identify plurality of parameters value of the captured image and to compare the identified parameters value with a predetermined parameters value to identify IOP of the eye. The predetermined parameters value is determined during a calibration. A storage unit is configured in the control unit to store the calibrated predetermined parameters value.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The features of the present disclosure are set forth with particularity in the appended claims. The disclosure itself, together with further features and attended advantages, will become apparent from consideration of the following detailed description, taken in conjunction with the accompanying drawings. One or more embodiments of the present disclosure are now described, by way of example only, with reference to the accompanied drawings wherein like reference numerals represent like elements and in which:

The figures depict embodiments of the disclosure for purposes of illustration only. One skilled in the art will readily recognize from the following description that alternative embodiments of the structures and methods illustrated herein may be employed without departing from the principles of the disclosure described herein.

DETAILED DESCRIPTION

The foregoing has broadly outlined the features and technical advantages of the present disclosure in order that the detailed description of the disclosure that follows may be better understood. Additional features and advantages of the disclosure will be described hereinafter which form the subject of the claims of the disclosure. It should be appreciated by those skilled in the art that the conception and specific embodiment disclosed may be readily utilized as a basis for modifying or designing other structures for carrying out the same purposes of the present disclosure. It should also be realized by those skilled in the art that such equivalent constructions do not depart from the spirit and scope of the disclosure as set forth in the appended claims. The novel features which are believed to be characteristic of the disclosure, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

The present disclosure relates to a method to identify Intraocular Pressure (IOP) of an eye by blowing air onto an eye ball of the eye. The method comprises of placing a foil-flap support assembly between an imaging unit and the eye, wherein the foil-flap support assembly has a transparent stiff foil fixed to a support and plurality of movable flaps facing the eye is suspended from the support. Once the foil-flap support assembly is placed, air of predetermined amount of pressure, which is in the range of 10 millimeter of Mercury (10 mmHg) to 100 millimeter of Mercury (100 mmHg), is blown onto an eye ball of the eye through an air channel. The blown air hits the eye ball. The blown air rebounds from the eye ball deflating the flaps of the foil-flap support assembly. At this stage an image of the deflated foil-flap support assembly is captured and plurality of parameters value of the captured image is calculated. The plurality of parameters value of the is selected from at least one of size, length, breadth, width, shape, lateral shifts, rotation, translation, scaling or any combinations thereof. Now, the calculated parameters value is compared with plurality of predetermined parameters value to identify IOP of the eye.

The predetermined parameters value is determined from a normal eye by performing a calibration comprising steps of placing the foil-flap support assembly between the eye and the camera. At this stage, an image of the foil-flap support assembly is captured. The plurality of parameters value of the captured image is calculated. Now, air of the predetermined amount of pressure is blown onto an eye ball of the normal eye through the air channel. The air blown hits the eye ball and gets rebound from the eye ball which deflates the foil-flap support assembly. Now, the image of the deflated flaps of the foil-flap support assembly is captured. From the captured image, the plurality of parameters value of the deflated flaps is calculated. The calculated parameters value is stored. Later, the amounts of air pressure are varied and are blown to the eye ball of the normal eye. The images of the deflated flaps corresponding to varied amounts of air pressure are captured. The parameters value is calculated for each captured images and is stored.

A system to identify IOP of the eye is disclosed as another aspect of the present disclosure. The system comprises a foil-flap support assembly and a control unit. The foil-flop support assembly comprises a transparent stiff foil fixed to a support and plurality of movable flaps facing the eye is flexibly suspended from the support. The transparent stiff foil and the plurality of movable flaps have a thickness in the range of 0.1 millimeter to 5.0 millimeter. Also, they have a predefined color or prerequisite pattern different from one another. The control unit comprises a blowing unit, a camera, a computing device and a storage unit. The air channel selected from at least one of a transparent tube and a non-transparent tube. The transparent tube is selected from at least one of a glass tube, plastic tube and rubber tube. The non-transparent tube is selected from at least one of plastic tube, rubber tube and metallic tube. The air channel is used to blow air of predetermined amount of pressure onto an eye ball of the eye. The air channel is placed at a distance of 30 millimeter to 40 millimeter from the eye. The blown air hits the eye ball and gets rebound from the eye ball deflating the flaps of the foil-flap support assembly. The control unit also includes an imaging unit used to capture image of the foil-flap support assembly before and after deflation of the flaps. The computing device is configured to identify plurality of parameters value of the captured image and to compare the identified parameters value with a predetermined parameters value to identify IOP of the eye. The predetermined parameters value is determined during a calibration. The storage unit is configured in the control unit to store the calibrated predetermined parameters value.

Figure 1A:
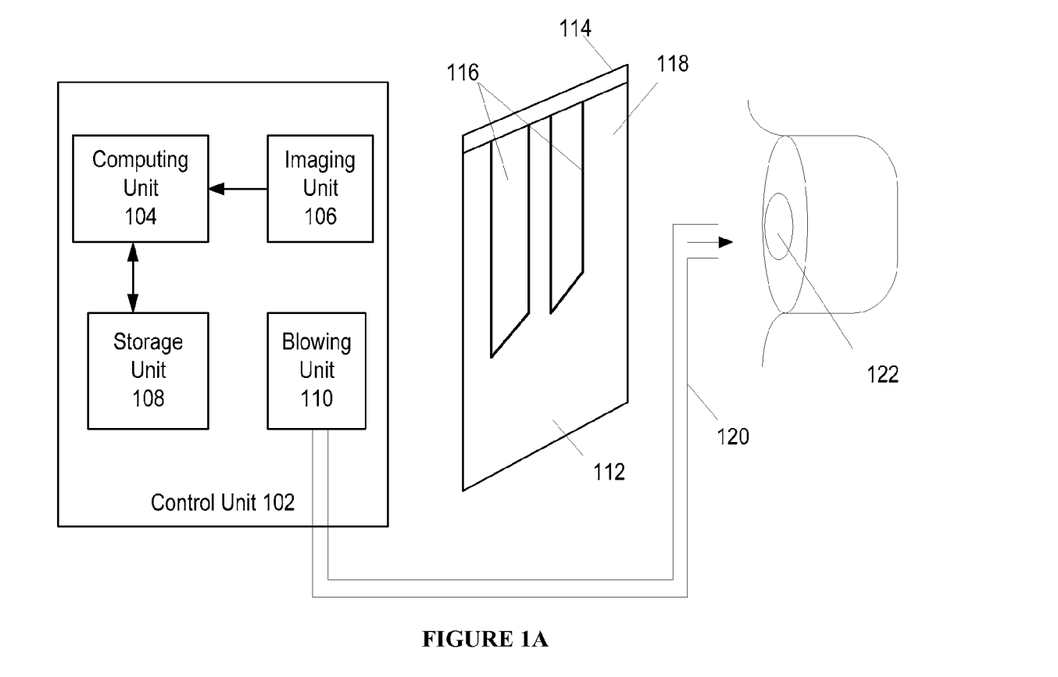
FIG. 1A shows an exemplary system to identify IOP of the eye according to an embodiment of the present disclosure.

FIG. 1A shows a system to identify IOP of the eye according to an embodiment of the present disclosure. The system has a foil-flap support assembly 112 and a control unit 102. The foil-flap assembly have a transparent stiff foil 118 fixed to a support 114 and plurality of movable flaps 116 facing an eye is flexibly suspended from the support 114. The transparent stiff foil 118 and the plurality of movable flaps 116 have a thickness in the range of 0.1 millimeter to 5.0 millimeter. Also, the transparent stiff foil 118 and the plurality of movable flaps 116 have a predefined color or prerequisite pattern different from one another. The control unit 102 comprises a blowing unit 110, a imaging unit 106, a computing unit 104 and a storage unit 108. The blowing unit 110 has an air channel 120 to blow air of predetermined amount of pressure onto an eye ball 122 of the eye. The air channel 120 is placed such a way that it impinges air on the eye ball 122 and do not block rebound air that deflates the suspended flaps 116. In an embodiment, the air channel 120 comprises a nozzle with one or more openings. The opening of the air channel 120 can be of any shape including but not limited to circle, oval etc. In an exemplary embodiment, one or more sensors can be placed between or around the opening to measure the reflected air pressure. The imaging unit 106 is used to capture image of the foil-flap support assembly 112 before (in calibration) and after deflation. The computing device 104 is configured to identify plurality of parameters value of the captured image and to compare the identified parameters value with a predetermined parameters value which is determined during a calibration to identify IOP of the eye. The storage unit 108 is used to store calibrated parameters value.

Figure 1B:
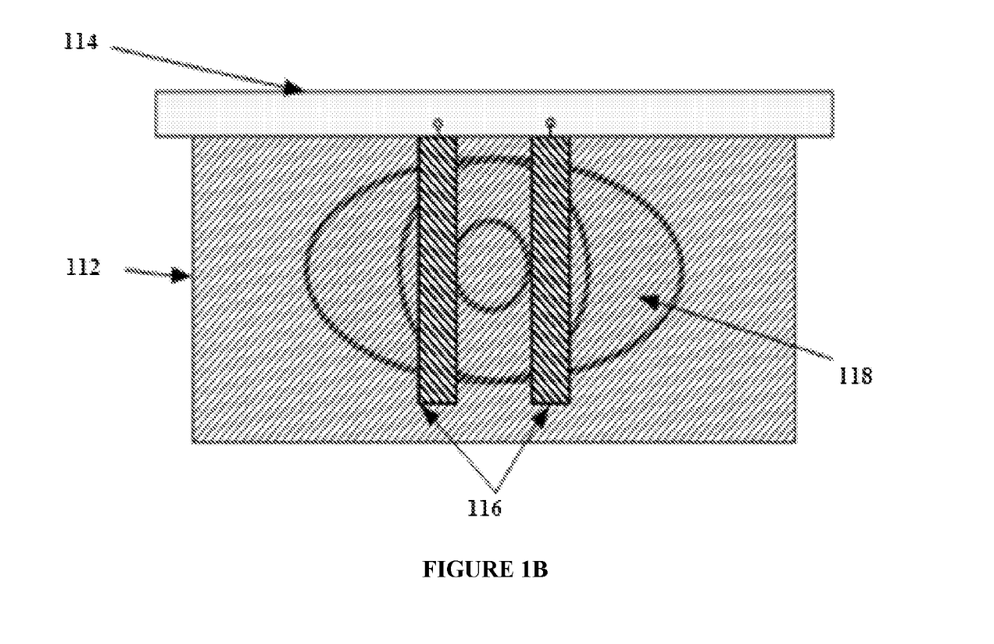
FIG. 1B shows arrangement of various components of an assembly according to an embodiment of the present disclosure.

FIG. 1B shows arrangement of various components of an assembly 112 according to an embodiment of the present disclosure. A black or any specific colored definite fringe pattern on the transparent material labelled 118 is rigidly fixed to the support 114. Further, two or more flaps 116 with another definite fringe pattern like moiré pattern or any other definite pattern is flexibly suspended from the support 114 that gets deflated as rebound air hits on them. This assembly 112 is placed between the imaging unit 106 and the eye such that the images of the combined fringe pattern can be captured without air puffing and while is puffed. As the rebound air falls on the suspended flaps 116 could either moved laterally apart from each other or could be made moved front to back direction. Both the described movements will change the parameters value such as breadth, length and lateral shifts. This change in parameters value is directly proportional to rebound air pressure.

Figure 2A:
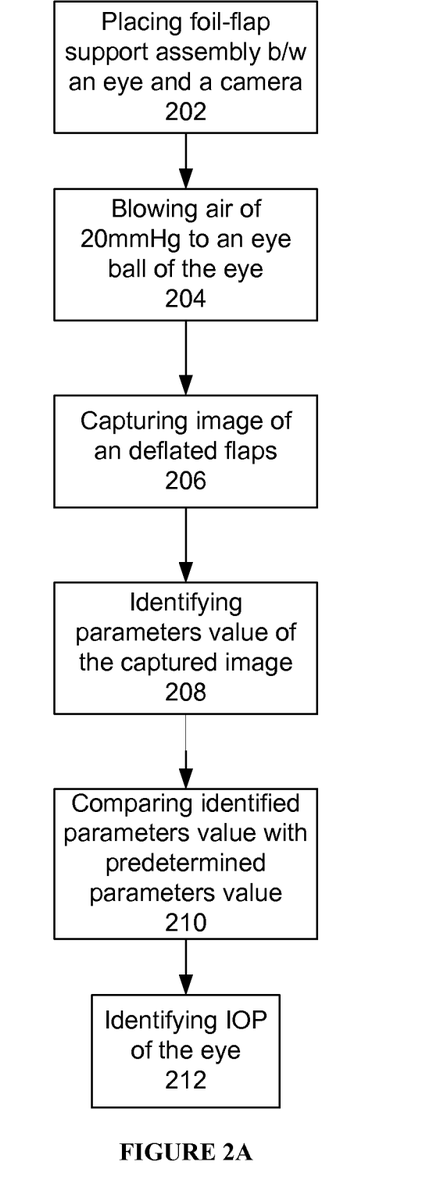
FIG. 2A illustrates an exemplary logical steps used to identify Intraocular Pressure (IOP) of an eye according to an embodiment of present disclosure.
Figure 2B:
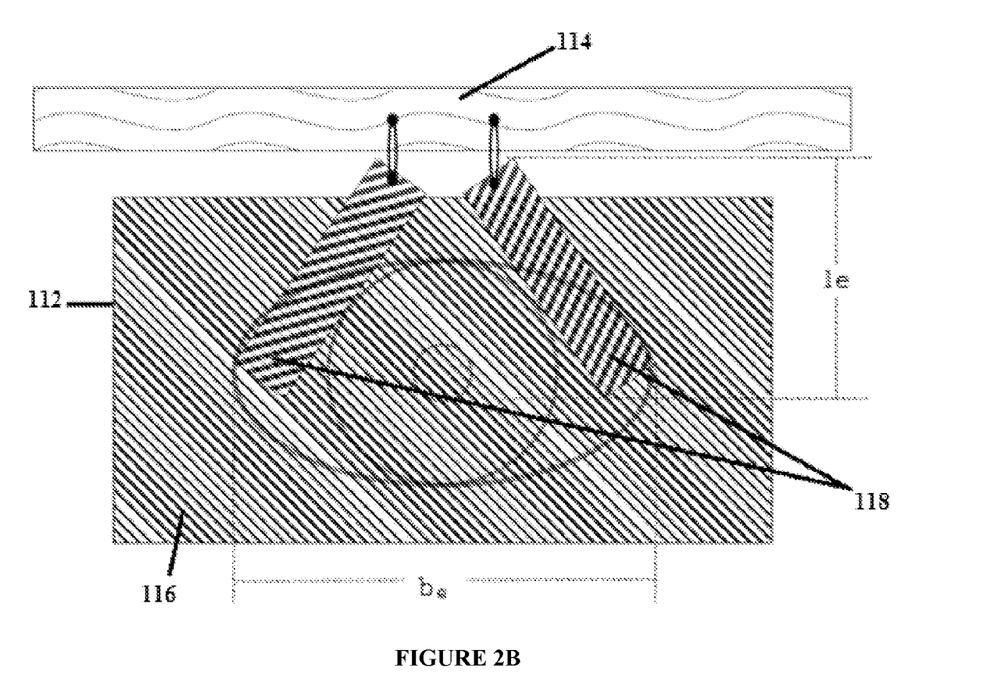
FIG. 2B is an exemplary image illustrating deflation of flaps according to an embodiment of the present disclosure.

FIG. 2A illustrates a method to identify Intraocular Pressure (IOP) of an eye according to an embodiment of present disclosure. The method comprises acts of placing a foil-flap support assembly 112 between the eye and a imaging unit 106 at step 202, wherein the foil-flap support assembly has a transparent stiff foil 118 fixed to a support 114 and plurality of movable flaps 116 facing the eye is suspended from the support 114. At step 204 the air of predetermined amount of pressure i.e. of 20 millimeter of Mercury (20 mmHg) is blown onto an eye ball 122 of the eye through an air channel 120. The air blown to the eye ball 122 gets rebound from the eye ball 122 deflating the flaps 116 of the assembly 112. At step 206 an image of the deflated flaps 116 of the foil-flap support assembly 112 is captured by the imaging unit 106. The plurality of parameters value of the captured image is identified at step 208 by a computing unit 104. For example, in FIG. 2B, the length of the deflated flaps is labelled as $l_e$ and breadth of the flaps labelled as $b_e$ are identified at step 208. At step 110, the identified parameters value is compared with plurality of predetermined parameters value to identify IOP of the eye.

Figure 3A:
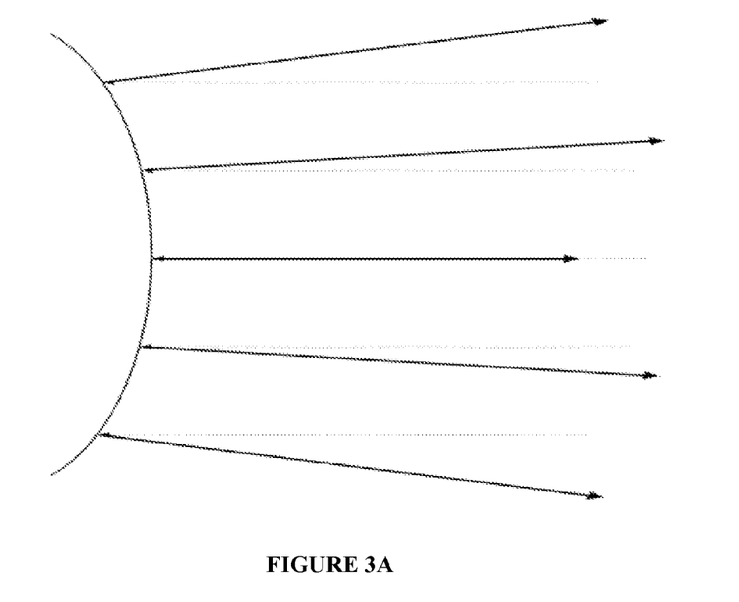
FIG. 3A shows an outwardly bulged lens surface of the eye when IOP is high according to an embodiment of the present disclosure.

FIG. 3A shows an outwardly bulged lens surface of the eye ball 122 when IOP is high according to an embodiment of the present disclosure. If the IOP is high, then the internal surface pressure is high that makes the lens surface bulged and inflexible or stiff as shown in FIG. 3A. When the air of 20 mmHg is blown on such surface, the air is outwardly rebounded from the eye ball 122 is less that depends on a surface curvature of the lens surface of the eye ball 122 of the eye which is usually bulged as shown. This makes the flexible flaps 116 to get less deflated and consequently there will be less change in parameters values.

Figure 3B:
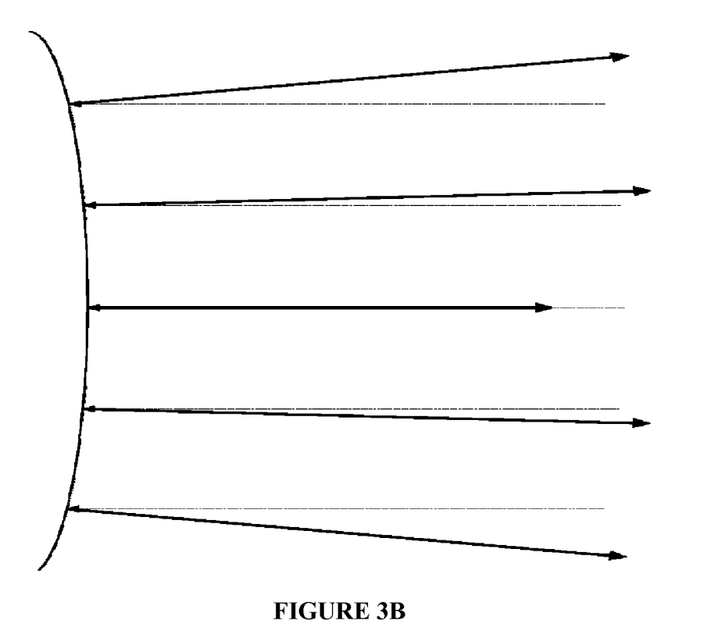
FIG. 3B shows a flat or inwardly dented lens surface of the eye when IOP is low according to an embodiment of the present disclosure.

FIG. 3B shows a flat or inwardly dented lens surface of the eye ball 122 when IOP is low according to an embodiment of the present disclosure. When the air at pressure of 20 mmHg is blown to the lens of the eye ball 122 having little or low IOP, the lens surface is flexible enough that allows external corneal surface of lens to become flat or dented inside. Further, the rebound air pressure is oriented in the direction of the flaps 116 would be more as shown in FIG. 3B.

Figure 4A:
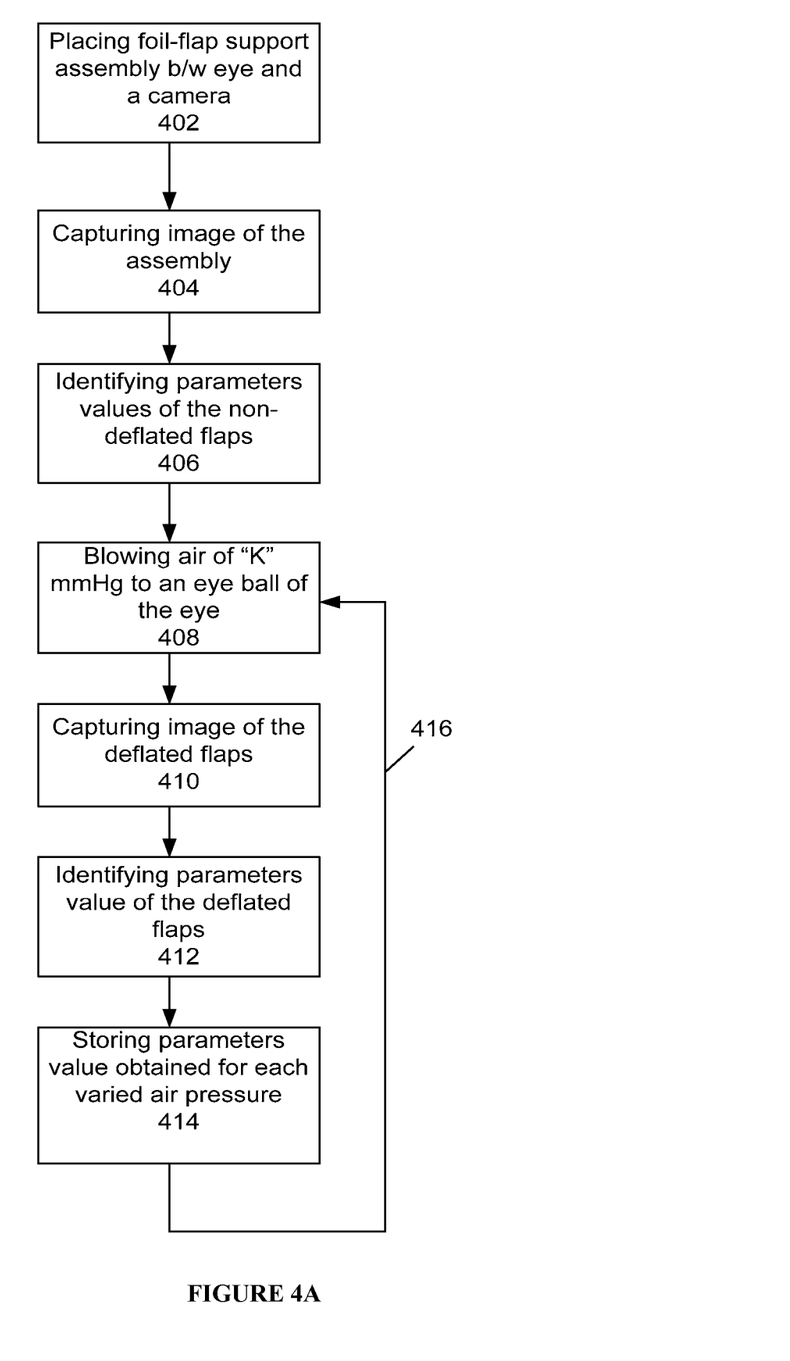
FIG. 4A illustrates an exemplary sequence of steps used for performing a calibration to determine predetermined parameters value from a normal eye according to an embodiment of the present disclosure.
Figure 4B:
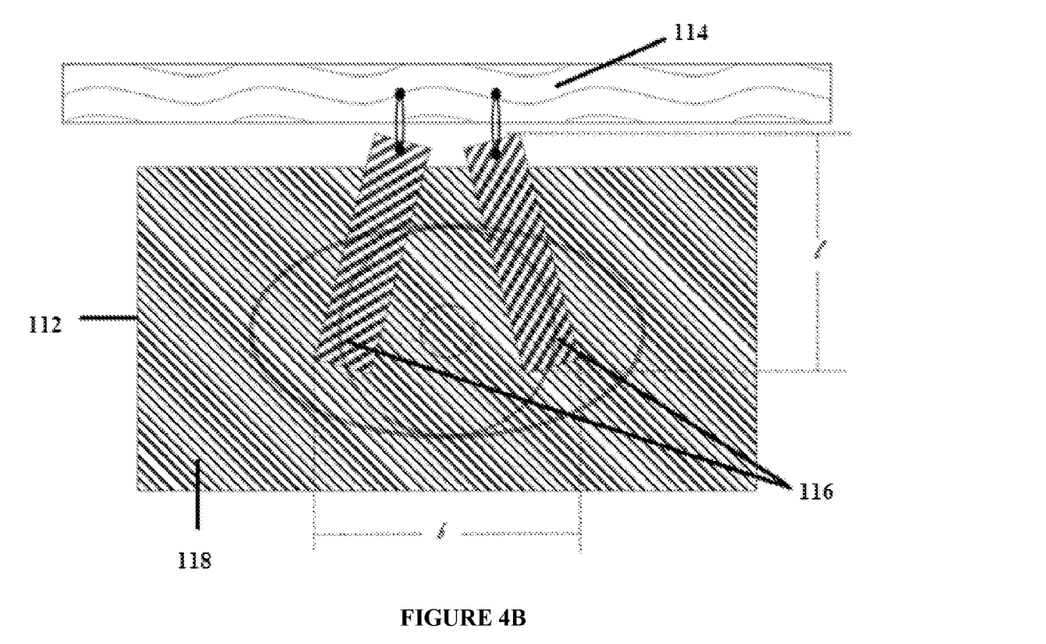
FIG. 4B is an image of the foil-flap support assembly before blowing the air in calibration according to an embodiment of the present disclosure.
Figure 4C:
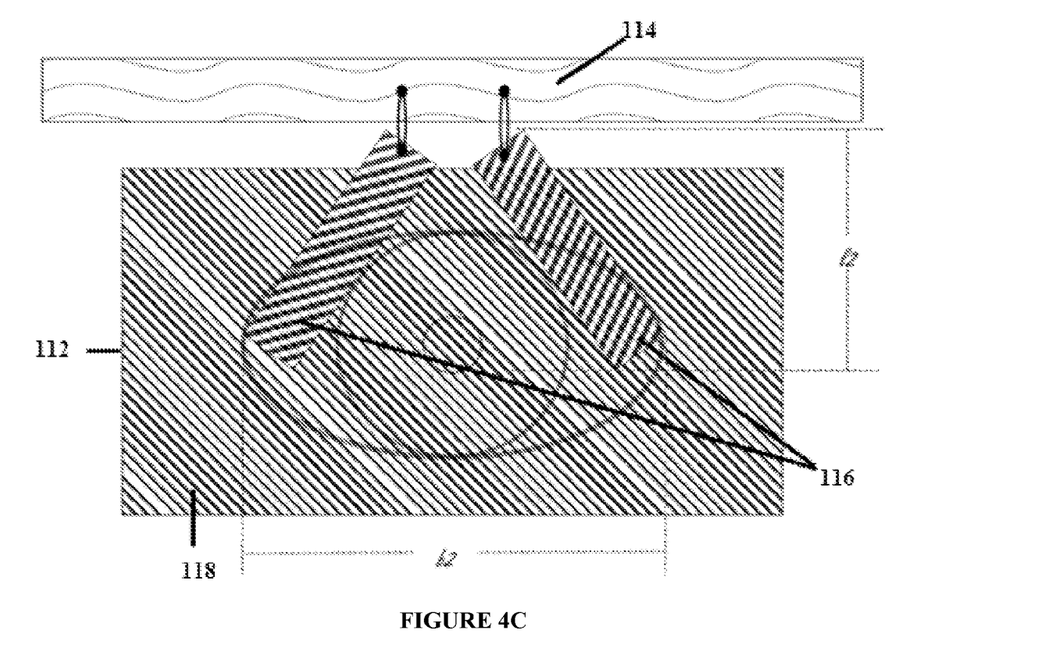
FIG. 4C is the image of the deflated flaps corresponding to varied amount of air pressure during calibration according to an embodiment of the present disclosure.

FIG. 4A illustrates a method of performing a calibration to determine predetermined parameters value from a normal eye according to an embodiment of the present disclosure. A foil-flap support assembly 112 is placed between the eye and the imaging unit 106 at step 402. At step 404, an image of the foil-flap support assembly 112 before the air is blown is captured using the imaging unit 106. The parameters values of the flaps 116 i.e. l and b as shown in FIG. 4B which are the length and breadth of the flaps before air is blown are identified at step 406. At step 408, air of 'K' mmHg amount of pressure is blown onto the eye ball 122. This causes the flaps 116 to get deflated since air blown gets rebound from the eye ball 122. The imaging unit 106 captures the image of the deflated flaps at step 410. The computing unit 104 identifies image parameters value of the deflated flaps 116 at step 412 i.e. $l_2$ and $b_2$ which are the length and breadth of the deflated flaps as shown in FIG. 4C. The storage unit 108 stores identified parameters value performed at step 414. The amounts of air pressure are varied and are blown to the eye ball 122 of the normal eye. The images of the deflated flaps 116 corresponding to varied amounts of air pressure are captured. The parameters value is calculated for each captured images and is stored in a storage unit 108.

Figure 5A:
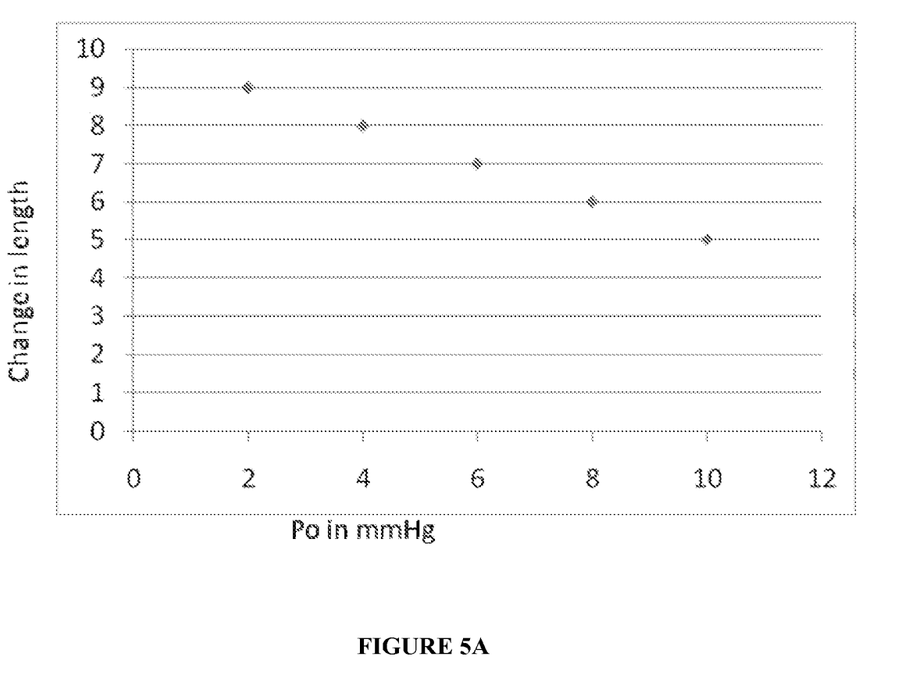
FIGS. 5A and 5B shows a relationship curves between varying amounts of air pressure $P_o$ and change in length $\Delta_l$ and change in breadth $\Delta_b$ respectively according to an embodiment of the present disclosure.

FIG. 5A is a relationship curve obtained during calibration between varying amounts of air pressure $P_o$ and change in length $\Delta_l$ according to an embodiment of the present disclosure. Here, the change in length is obtained by computing:
$\Delta_l = l - l_2$ where $\Delta_l$ is the change in length corresponding to varied amount of air pressure $P_o$.

Figure 5B:
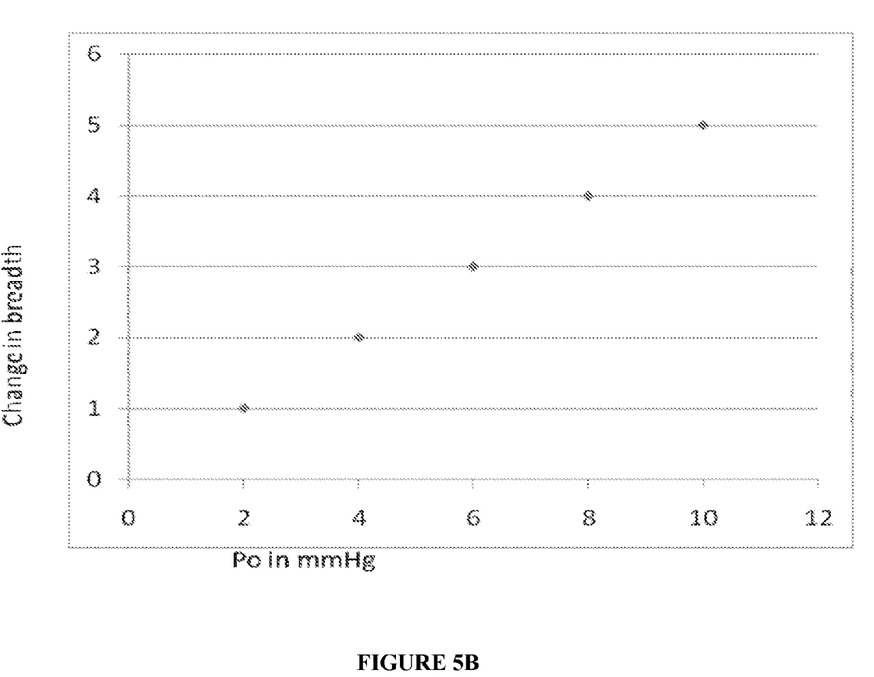

FIG. 5B is the relationship curve obtained during calibration between varying amounts of air pressure $P_o$ and change in breadth $\Delta_b$ according to an embodiment of the present disclosure. Here, the change in breadth is obtained by computing:
$\Delta_b = b - b_2$ where $\Delta_b$ is the change in breadth corresponding to varied amounts of air pressure $P_o$.

Additional features and advantages are realized through various techniques provided in the present disclosure. Other embodiments and aspects of the disclosure are described in detail herein and are considered as part of the claimed disclosure.

The present disclosure addresses a problem of integrating the Tonometer and Retina imaging into single device by making use of common resources and components.

The image analysis based intraocular pressure measurements facilitate in utilizing the resources optimally that aid in reducing cost and making device more portable.

Further, the proposed disclosure is a non-contact and non-evasive indirect approach, which is based on image analysis and the intraocular pressure determination explored based on prior calibration.

The intraocular pressure measured using the method disclosed in the present disclosure is used as a parameter by the ophthalmologist to diagnose glaucoma impairment of human beings.

| Reference Numeral | Description |
| --- | --- |
| 102 | Control Unit |
| 104 | Computing Unit |
| 106 | Imaging Unit |
| 108 | Storage Unit |
| 110 | Blowing Unit |
| 112 | Foil-flap Support Assembly |
| 114 | Support |
| 116 | Movable Flaps |
| 118 | Transparent Foil |
| 120 | Air Channel |
| 122 | Eye ball |

We claim:

1. A method to identify Intraocular Pressure (IOP) of an eye, said method comprising acts of:
   placing a foil-flap support assembly between an imaging unit and the eye, wherein the foil-flap support assembly has a transparent stiff foil fixed to a support and plurality of movable flaps suspended from the support facing the eye;
   blowing air of predetermined amount of pressure onto an eye ball of the eye through an air channel, wherein the air blown to the eye ball rebounds from the eye ball deflecting the flaps of the support assembly;
   capturing an image of the deflected foil-flap support assembly;
   identifying plurality of parameters value of the captured image; and comparing the plurality of parameters value with plurality of predetermined parameters value to identify IOP of the eye.

2. The method as claimed in claim 1, wherein the predetermined amount of air pressure is in the range of 10 millimeter of Mercury (10 mmHg) to 100 millimeter of Mercury (100 mmHg).

3. The method as claimed in claim 1, wherein the plurality of parameters value of the captured image is selected from at least one of size, length, breadth, width, shape, lateral shifts, rotation, translation, scaling or any combinations thereof.

4. The method as claimed in claim 1, wherein the predetermined parameters value is determined from a normal eye by performing a calibration comprising steps of:
   a) placing the foil-flap support assembly between the eye and the imaging unit;
   b) capturing the image of the foil-flap support assembly;
   c) identifying the plurality of parameters value of the image;
   d) blowing the predetermined amount of air pressure through the air channel of a blowing unit onto an eye ball of the normal eye, wherein the air blown to the eye ball rebounds from the eye ball deflecting the foil-flap support assembly;
   e) capturing the image of the deflected foil-flap support assembly;
   f) identifying the plurality of parameters value of the image obtained from the step e);
   repeating the steps d), e) and f) for plurality of varying predetermined amount of air pressure; and
   storing the parameters value obtained for each varied air pressure.

5. A system to identify Intraocular Pressure (IOP) of an eye comprising:
   a foil-flap support assembly comprising:
      a transparent stiff foil fixed to a support; and
      plurality of movable flaps flexibly facing an eye suspended from the support;
   a control unit comprising:
      a blowing unit having an air channel to blow air of predetermined amount of pressure on to an eye ball of the eye;
      an imaging unit to capture image of the foil-flap support assembly before and after deflection;
      a computing device to identify plurality of parameters value of the captured image and to compare the identified parameters value with a predetermined parameters value determined during a calibration to identify IOP of the eye; and
      a storage unit to store calibrated parameters value.

6. The system as claimed in claim 5, wherein the air channel is placed at a distance of 30 millimeter to 40 millimeter from the eye.

7. The system as claimed in claim 6, wherein the air channel is selected from at least one of a transparent tube and non-transparent tube.

8. The system as claimed in claim 7, wherein the transparent tube is selected from at least one of a glass tube, plastic tube and rubber tube.

9. The system as claimed in claim 7, wherein the non-transparent tube is selected from at least one of a glass tube, plastic tube and metallic tube.

10. The system as claimed in claim 5, wherein the transparent stiff foil and the plurality of movable flaps has a thickness in the range of 0.1 millimeter to 5.0 millimeter.

11. The system as claimed in claim 5, wherein the transparent stiff foil and the plurality of movable flaps have a predefined color or prerequisite pattern different from one another.

12. The system as claimed in claim 5, wherein the air channel comprises one or more openings of shape selected from circle and oval.

13. The system as claimed in claim 5, wherein the one or more openings comprises at least one sensor to measure the reflected air pressure.

14. The system as claimed in claim 10, wherein the transparent stiff foil and the plurality of movable flaps have a predefined color or prerequisite pattern different from one another.

\* \* \* \* \*